United States Patent [19]

Kitamura

[11] Patent Number: 5,272,776
[45] Date of Patent: Dec. 28, 1993

[54] BED SYSTEM FOR CT SCANNER

[75] Inventor: Koji Kitamura, Tokyo, Japan

[73] Assignee: Kabushiki Kaisha Toshiba, Kawasaki, Japan

[21] Appl. No.: 563,616

[22] Filed: Aug. 7, 1990

[30] Foreign Application Priority Data

Aug. 9, 1989 [JP] Japan .................. 1-204709

[51] Int. Cl.⁵ .............................................. A61G 7/08
[52] U.S. Cl. ........................................ 5/81.1; 5/600
[58] Field of Search ............. 5/60, 81 R, 81 B, 600, 5/81.1; 269/322

[56] References Cited

U.S. PATENT DOCUMENTS

| | | | |
|---|---|---|---|
| 1,829,274 | 10/1931 | Gilroy | 5/81 B |
| 3,944,204 | 3/1976 | Cesar | 269/323 |
| 4,131,802 | 12/1978 | Braden et al. | 269/322 |
| 4,225,125 | 9/1980 | Lee | 269/322 |
| 4,613,122 | 9/1986 | Manabe | 269/322 |
| 4,641,823 | 2/1987 | Bergman | 269/322 |
| 4,669,137 | 6/1987 | Schnelle et al. | 5/81 R |
| 4,671,728 | 6/1987 | Clark et al. | 5/81 R |
| 4,773,637 | 9/1988 | Jarin | 269/322 |
| 4,833,972 | 5/1989 | Bohusch et al. | 269/322 |
| 4,944,501 | 7/1990 | Sireul et al. | 269/322 |
| 4,984,774 | 1/1991 | Zupancic et al. | 269/322 |

FOREIGN PATENT DOCUMENTS 0200374 12/1986 European Pat. Off. .

Primary Examiner—Peter M. Cuomo
Assistant Examiner—Michael J. Milano
Attorney, Agent, or Firm—Cushman, Darby & Cushman

[57] ABSTRACT

A bed system, for a CT scanner such as an MRI apparatus having a frame with an imaging space therein, in which rollers support a bed plate for carrying a body to be examined, and the bed plate is moved by a driver into and out of the imaging space of the frame.

11 Claims, 4 Drawing Sheets

BED SYSTEM FOR CT SCANNER

BACKGROUND OF THE INVENTION

1. Field of the Invention

The present invention relates to a medical bed system, and more particularly to a bed system for carrying a body designated for examination into an imaging space of a CT scanner such as an MRI CT scanner or an X-ray CT scanner.

2. Description of the Background Art

In a conventional CT scanner such as an MRI (Magnetic Resonance Imaging) apparatus, a magnet frame, which includes a CT scanner is formed separately from a bed unit. The magnet frame is fairly long even in comparison to the bed unit. A body to be examined is carried on a bed plate that attaches to the bed unit and is subsequently placed in a proper scanning position of the magnet frame by removing the bed plate from the bed unit, and properly positioning the bed plate upon the magnet frame. Hence, the bed plate has a long stroke in the bed unit.

Accordingly, in the conventional bed unit for the MRI apparatus, long the stroke of the bed plate together with a long bed unit, requires a large space for installation.

SUMMARY OF THE INVENTION

Accordingly, it is an object of the present invention to provide a bed system for a CT scanner, such as an MRI apparatus which is, free from the aforementioned disadvantages and inconveniences of the prior art, and minimizes installation space.

In accordance with one aspect of the present invention, there is provided a bed system for a CT scanner having a frame with an imaging space therein. The bed system comprises a bed, plate for carrying a body to be examined, which can be moved into and out of the CT scanner imaging space of the frame by a drive means, and roller support means for supporting the bed plate.

BRIEF DESCRIPTION OF THE DRAWING

The above and other objects, features and advantages of the present invention will be apparent from the following description of the preferred embodiments with reference to the accompanying drawings, in which.

DESCRIPTION OF THE PREFERRED EMBODIMENTS

Figure 1:
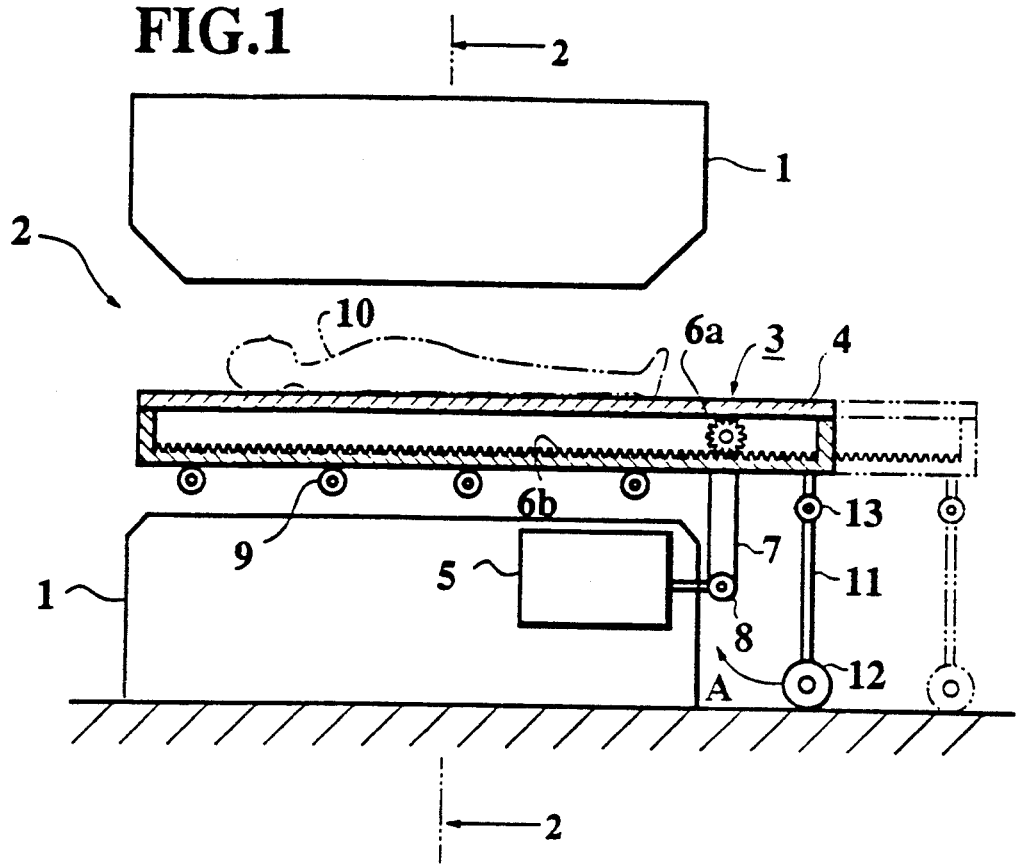
FIG. 1 is a central longitudinal cross section of a first embodiment of a bed system for a CT scanner according to the present invention.
Figure 2:
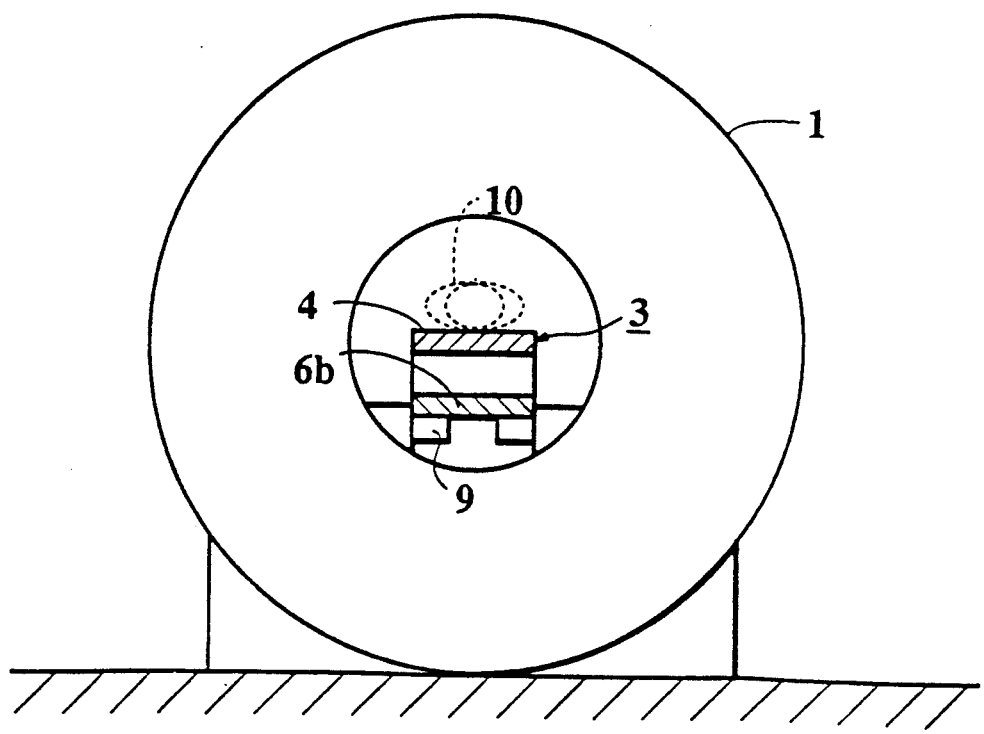
FIG. 2 is a cross sectional view, taken along the line 2—2 in FIG. 1.

Referring now to the drawings, wherein like reference characters designate like or corresponding parts throughout the several views and thus the repeated description thereof can be omitted for the sake of brevity, there is schematically shown in FIGS. 1 and 2 a first embodiment of a bed system for an MRI (magnetic resonance imaging) apparatus.

In the drawings, a magnet frame 1 is provided with an MRI CT scanner (not shown) therein, the CT scanner includes a main magnet for generating static magnetic field, gradient coils for generating gradient fields, an RF coil for irradiating excitation fields and detecting NMR signals, and so forth. The magnet frame 1 includes an MRI imaging space 2 in its central portion.

A bed system 3 is combined with the magnet frame 1. The bed system 3 is provided with a bed box structure having a bed plate 4 for carrying a subject body 10 designated for examination a on its top surface and a combination of pinion and rack gears 6a and 6b engaged with each other, which are mounted under the bed plate 4, and a driver 5 arranged in the magnet frame 1, for moving the bed box structure into and out of the imaging space 2 of the magnet frame 1. A drive wheel 8 is mounted on a drive shaft of the driver 5, and a chain or belt 7 is extended between the pinion gear 6a and the drive wheel 8 for transmitting the driving force of the driver 5 to the rack gear 6b.

The bed box structure is supported by multiple rollers 9 rotatably mounted in the magnet frame 1. Legs 11 are provided on the front bottom end of the bed box structure, and a caster 12 is mounted on the bottom of each leg 11. A hinge 13 is arranged in the upper part of each leg 11 so as to fold the lower major portion of the leg 11 into the space under the bed box structure, as indicated by an arrow A in FIG. 1. In this embodiment, by driving the driver 5, the driving force is transmitted from the driver 5 to the pinion and rack gears 6a and 6b to move the bed box structure along with the bed plate 4 carrying the body 10 into or out of the imaging space 2 of the magnet frame 1.

In this embodiment, oil pressure, air pressure and an electric motor can be used as a power source for the driver 5, and any such power source should not affect or influence, nor be affected or influenced by, the magnetic field of the CT scanner. For instance, a ultrasonic wave motor may be conveniently used as the power source, and gears of the driving portions may be preferably made of stainless steel. The chain or belt 11 should not also affect or receive any influence to or from the magnetic field of the CT scanner. The chain or belt 11 may be preferably made of rubber or the like. Further, the driver 5 may be arranged within the bed box structure.

As described above, in this embodiment, since the bed system 3 is assembled within the CT scanner, such as the MRI apparatus, there is no need to provide a separate bed unit outside the magnet frame 1, and hence the installation space and size of the whole system including the CT scanner and the bed system can be largely reduced.

Figure 3:
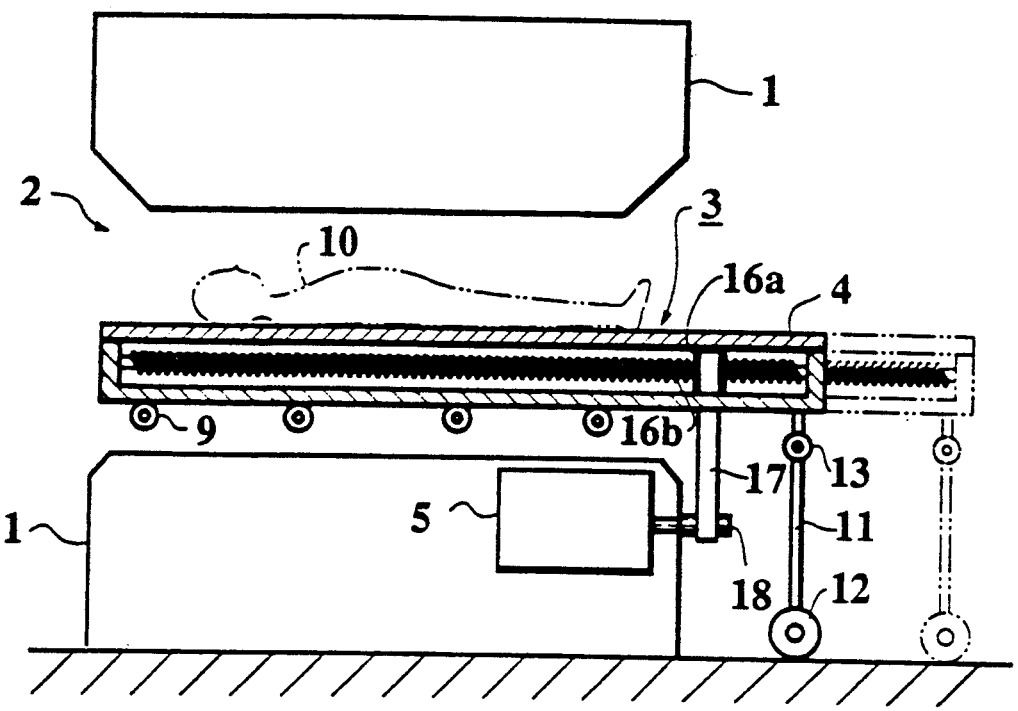
FIG. 3 is a central longitudinal cross section of a second embodiment of a bed system for a CT scanner according to the present invention.

In FIG. 3, there is shown a second embodiment of a bed system for an MRI apparatus, having the same structure as the first embodiment shown in FIG. 1, except that a lead screw structure comprising a female screw member 16a and a male screw rod member 16b engaged therewith are used, and that a drive wheel 18 is mounted on a drive shaft of the driver 5, and a chain or belt 17 is extended between the female screw member 16a and the drive wheel 18. In this embodiment, the same effects and advantages as those of the first embodiment are obtained.

Figure 4:
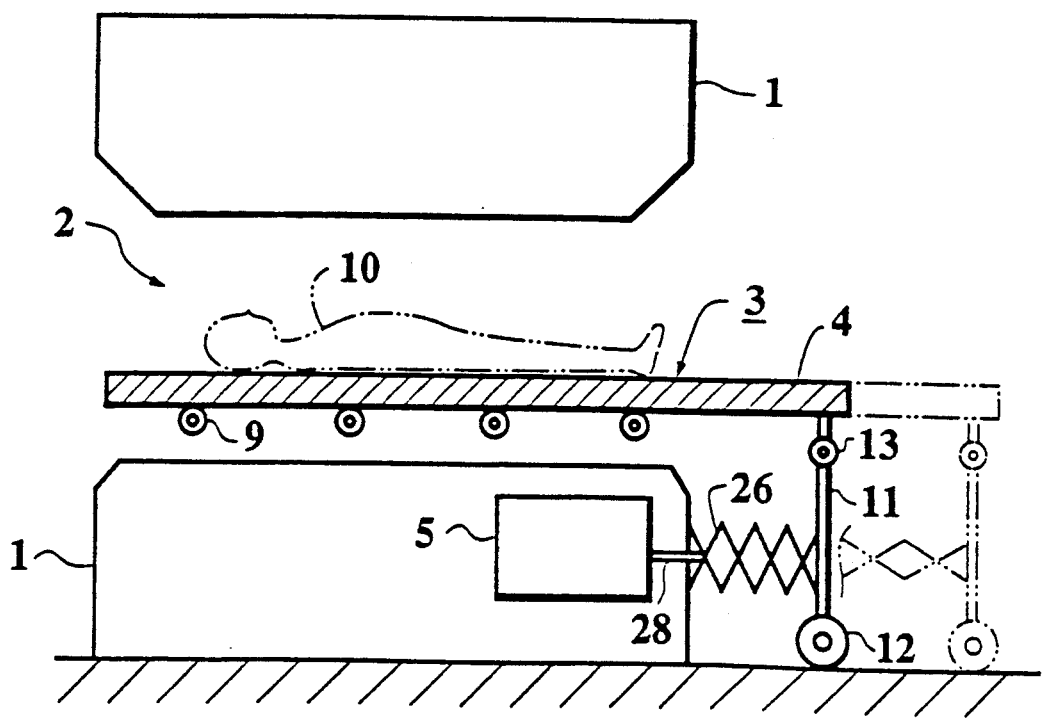
FIG. 4 is a central longitudinal cross section of a third embodiment of a bed system for a CT scanner according to the present invention.

In FIG. 4, there is shown a third embodiment of a bed system for an MRI apparatus, having the same structure as the first embodiment shown in FIG. 1, except that a bed plate 4 is provided instead of the bed box structure of the first embodiment, and that an extensible and foldable frame 26 is mounted between a slidable drive shaft 28 of the driver 5 and the legs 11. By projecting or retracting the slidable drive shaft 28 of the driver 5, the frame 26 is extended or folded to move the bed plate 4. In this embodiment, the same effects and advantages as those of the first embodiment are obtained.

Figure 5:
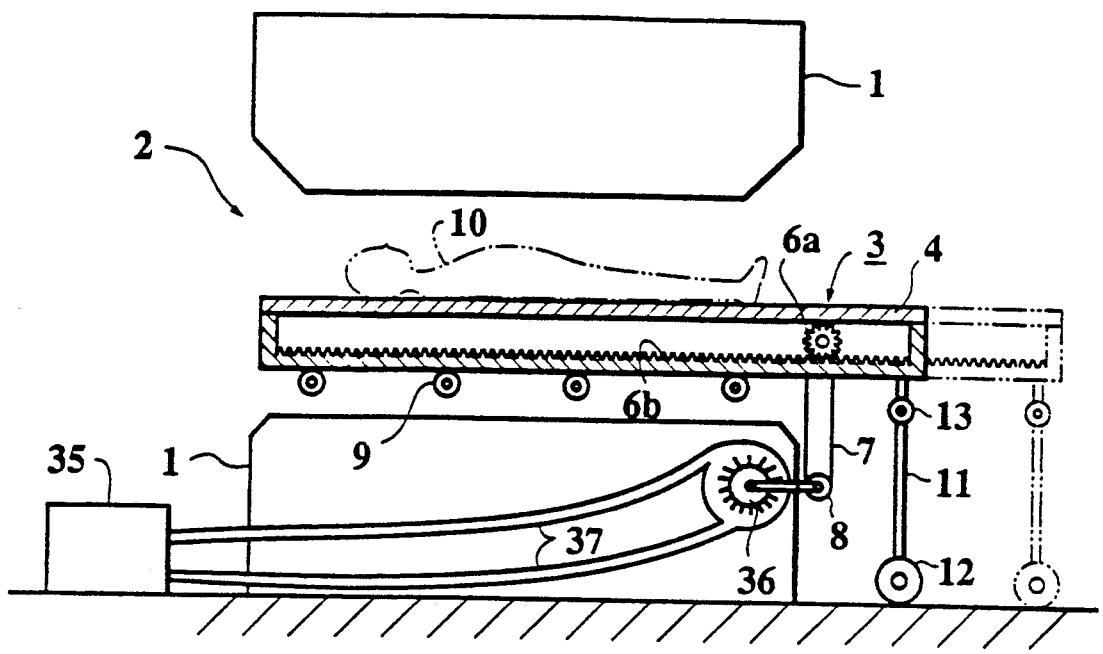
FIG. 5 is a central longitudinal cross section of a fourth embodiment of a bed system for a CT scanner according to the present invention.

In FIG. 5, there is shown a fourth embodiment of a bed system for an MRI apparatus, having the similar structure to the first embodiment shown in FIG. 1. In this embodiment, in order to absolutely remove or reduce the influence of the magnetic field on the power source, a motor pump 35 is installed outside the magnet frame 1, and a vane-wheel 36 is arranged in the magnet frame 1, for driving the drive wheel 8, and is connected to the motor pump 35 via tubes 37. The vane-wheel 36 is driven by either hydraulic or air pressure. In this embodiment, the same effects and advantages as those of the first embodiment obtained.

Figure 6:
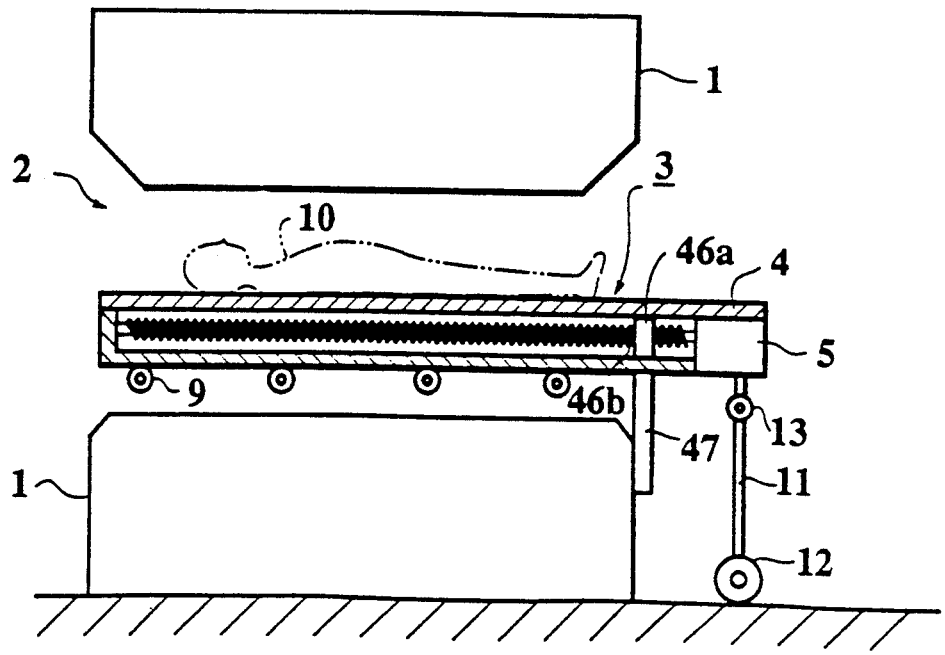
FIG. 6 is a central longitudinal cross section of a fifth embodiment of a bed system for a CT scanner according to the present invention.

In FIG. 6, there is shown a fifth embodiment of a bed system for an MRI apparatus, having the similar structure to the second embodiment shown in FIG. 3. In this embodiment, a lead screw structure comprising a female screw member 46a and a male screw rod member 46b engaged therewith are arranged in the bed box structure in the same manner as the second embodiment, and the driver 5 is arranged in the front end portion of the bed box structure and is connected to a male screw rod member 46b for directly driving the same. The female screw member 46a is mounted to the magnet frame 1 through a bracket 47. In this embodiment, the same effects and advantages as those of the second embodiment are obtained.

Figure 7:
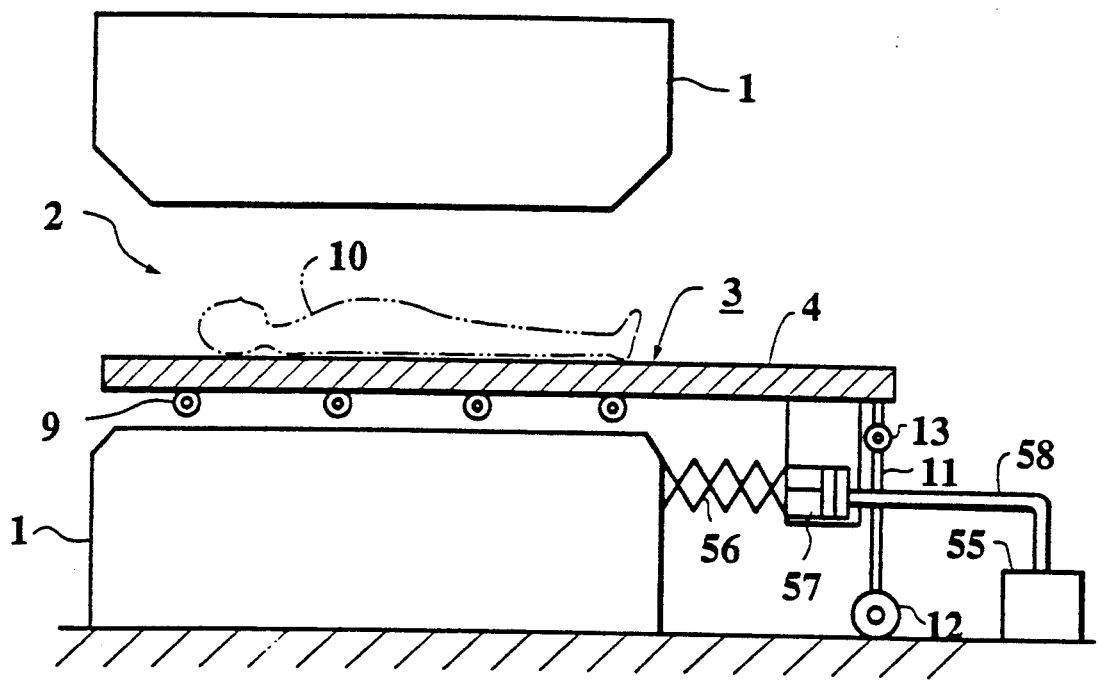
FIG. 7 is a central longitudinal cross section of a sixth embodiment of a bed system for a CT scanner according to the present invention.

In FIG. 7, there is shown a sixth embodiment of a bed system for an MRI apparatus, having the similar structure to the third embodiment shown in FIG. 4. In this embodiment, a cylinder device 57 is mounted under the front end portion of the bed plate 4, and an extensible and foldable frame 56 is mounted between the front end of the magnet frame 1 and an actuating end of the cylinder device 57. A pump 55 is connected to the cylinder device 57 through a hydraulic pressure hose 58. In this embodiment, the same effects and advantages as those of the third embodiment are obtained.

Although the present invention has been described in its preferred embodiments with reference to the accompanying drawings, it it readily understood that the present invention is not restricted to the preferred embodiments and that various changes and modifications can be made by those skilled in the art without departing from the spirit and scope of the present invention.

What is claimed is:

1. A bed system for a CT scanner having a frame with an imaging space therein, comprising:
   a bed plate for carrying a body to be examined, the bed plate being movable into and out of the imaging space of the frame;
   legs continuously attached to a fixed location on a front end portion of the bed plate as the bed plate is moved into and out of the imaging space of the frame;
   roller support means, located within the imaging space of the frame, for supporting the bed plate as it is moved into and out of the imaging space of the frame; and
   drive means for moving the bed plate into and out of the imaging space of the frame;
   wherein the bed plate is supported fully by the legs and the roller support means so that when the bed plate is substantially entirely within the frame, substantially the entire bed system is contained within the frame except for the front end portion.

2. The bed system of claim 1, wherein the drive means includes a driver, a combination of rack and pinion gears arranged under the bed plate, and a transmission means for transmitting driving force of the driver to the rack and pinion gears, thereby moving the bed plate either into or out of the imaging space of the frame.

3. The bed system of claim 1, wherein each of the legs has a caster on a lower end.

4. The bed system of claim 2, wherein the driver is arranged within the frame.

5. The bed system of claim 2, wherein the driver is arranged under the bed plate.

6. The bed system of claim 1, wherein the drive means includes a driver, a combination of a female screw member and a male screw rod member engaging therewith, arranged under the bed plate, and transmission means for transmitting driving force of the driver to the female screw member and the male screw rod member.

7. The bed system of claim 1, wherein the drive means includes a driver having a slidable drive shaft, and an extensible and foldable frame mounted between the slidable drive shaft of the driver and a front end portion of the bed plate.

8. The bed system of claim 6, wherein the driver is arranged within the frame.

9. The bed system of claim 6, wherein the driver is arranged under the bed plate.

10. The bed system of claim 7, wherein the driver is arranged within the frame.

11. The bed system of claim 7, wherein the driver is arranged under the bed plate.

* * * * *